US005507281A

United States Patent [19]

Kuhnel et al.

[11] Patent Number: 5,507,281

[45] Date of Patent: Apr. 16, 1996

[54] DEVICE FOR INITIATING A MECHANICAL SWITCHING OPERATION IN SYNCHRONISM WITH THE BREATHING

[75] Inventors: Andreas Kuhnel, Oberursel; Gerhard Poss, Schriesheim; Jurgen Wittekind, Frankfurt; Dieter Hochrainer, Bingen, all of Germany

[73] Assignee: Boehringer Ingelheim KG, Germany

[21] Appl. No.: 199,168

[22] PCT Filed: Aug. 20, 1992

[86] PCT No.: PCT/EP92/01912

§ 371 Date: Feb. 22, 1994

§ 102(e) Date: Feb. 22, 1994

[87] PCT Pub. No.: WO93/03783

PCT Pub. Date: Mar. 4, 1993

[30] Foreign Application Priority Data

Aug. 22, 1991 [WO] WIPO .................... PCT/EP91/01593
Oct. 8, 1991 [DE] Germany .......................... 41 33 274

[51] Int. Cl.[6] .................................................. A61M 15/00

[52] U.S. Cl. ............................ 128/203.15; 128/203.23; 128/203.12

[58] Field of Search ...................... 128/204.26, 204.24, 128/203.24, 203.23, 203.15, 203.13, 203.19, 203.12

[56] References Cited

U.S. PATENT DOCUMENTS

| | | | |
|---|---|---|---|
| 2,587,215 | 2/1952 | Priestly | 128/203.15 |
| 3,900,138 | 8/1975 | Phillips | 222/340 |
| 3,921,637 | 11/1975 | Bennie et al. | 128/203.15 |
| 4,014,336 | 3/1977 | Mathes | 128/266 |
| 4,274,403 | 6/1981 | Struve | 128/203.15 |
| 4,414,972 | 11/1983 | Young et al. | 128/203.15 |
| 4,803,978 | 2/1989 | Johnson, IV et al. | 128/200.23 |
| 4,971,050 | 11/1990 | Bartos | 128/204.28 |
| 5,027,808 | 7/1991 | Rich et al. | 128/203.28 |
| 5,033,463 | 7/1991 | Cocozza | 128/203.23 |
| 5,239,992 | 8/1993 | Bougamont et al. | 128/203.13 |
| 5,347,999 | 9/1994 | Poss et al. | 128/203.23 |

FOREIGN PATENT DOCUMENTS

| | | |
|---|---|---|
| 0166294 | 1/1986 | European Pat. Off. . |
| 0363060 | 4/1990 | European Pat. Off. . |
| 2238505 | 2/1975 | France . |
| 2516387 | 5/1983 | France . |
| 2598918 | 11/1987 | France . |
| 1945257 | 3/1970 | Germany . |
| 2603163 | 8/1976 | Germany . |
| 2749629 | 5/1978 | Germany . |
| 2726934 | 1/1979 | Germany . |
| 3040641 | 5/1982 | Germany . |
| 3535561 | 5/1986 | Germany . |
| 3901963 | 8/1990 | Germany . |
| 2144997 | 3/1985 | United Kingdom . |
| 2165159 | 4/1986 | United Kingdom . |
| WO90/07351 | 7/1990 | WIPO . |
| WO92/04068 | 3/1992 | WIPO . |

*Primary Examiner*—Ren Yan
*Assistant Examiner*—V. Srivastava
*Attorney, Agent, or Firm*—Sterne, Kessler, Goldstein & Fox

[57] ABSTRACT

In a device for initiating a mechanical switching operation in inhalers, in synchronism with the breathing, a membrane like transmitter element (47) is provided which cooperates with a release mechanism (45, 46, 50) on a switching device (13, 19*c*, 22).

9 Claims, 2 Drawing Sheets

8
8a
31
38
361
40
11
36
39
27
7
41
32b
29
8
30
32
12a
37

32a
44
19
19b
45
22
19c
46
42
13
362
50
48
49
43
47

DEVICE FOR INITIATING A MECHANICAL SWITCHING OPERATION IN SYNCHRONISM WITH THE BREATHING

BACKGROUND OF THE INVENTION

1. Field of the Invention

The invention relates to a device for initiating a mechanical switching operation in synchronism with the breathing in inhalers having a membrane-like transmitter element.

2. Description of Related Art

Inhalers for administering inhaled preparations for therapy of the respiratory tract have been described in large numbers. In such devices, each actuation releases a specific dose of a pharmaceutical preparation. Depending on the type of device this preparation may be a micronised powder, an aqueous solution or a suspension of particles of the pharmaceutical (possibly a solution) in a liquified propellant gas. In any case, as the inhaler is actuated, an aerosol is produced from the pharmaceutical preparation. The production of the aerosol must be coordinated with the breathing so that the particles are well dispersed in the air breathed in and the particles reach the lower regions of the lung with the inspired air.

Some patients, particularly children and older people, frequently have difficulty in properly coordinating their breathing and the production of the aerosol.

To overcome these problems, various solutions have been proposed.

Apart from the possibility of initially spraying the aerosol into a container from which it is breathed in shortly afterwards (DE-A-2749629), the other devices have an apparatus which triggers the production of the aerosol in synchronism with the breathing, if the indrawn breath is sufficiently strong.

For an inhaler operated with propellant gas, DE-3040641 A1 describes a barrier which is supposed to be released by a sufficiently strong intake of breath at the mouth piece of the device, so that the aerosol can only be released when there is a strong enough suction produced by breathing in through the apparatus. However, there is a danger that the barrier will be jammed if the patient tries to trigger the jet of aerosol prematurely.

A propellant-free inhaler having the device described above for triggering a jet of aerosol in synchronism with the breathing is known from U.S. Pat. No. 3,921,637.

In the known inhaler, the transmitter element responding to the suction is a spring-balanced valve which is operatively connected via levers to a valve arrangement of the switching device. The valve arrangement is provided in the outlet line of a bellows pump which opens into a chamber containing capsules filled with the substance which is to be inhaled. The chamber in turn is connected to the outlet of the mouth piece.

When pressure is exerted manually on the pump bellows and the patient takes a strong breath inwards at the mouth piece, the valve responds to the suction produced in the mouth piece, moves forward and opens the valve via the levers in synchronism with the breathing. The pressure produced at the pump outlet generates a foreign air pulse which blows the dose of powder out of the capsule forming an aerosol which is then breathed in by the patient.

The known device has serious disadvantages. The transmitter device is of very complex construction and not easy to assemble. It consists of a plurality of very precisely machined components which have to be put together and adjusted in a complicated assembly process. Another serious disadvantage is the fact that the air breathed in flows through the inhaler and over the mechanical parts of the device. As a result, the depositing of dust and dirt on the precise bearings is unavoidable in the course of time. This may also occur, in particular, as a result of inhalers of this kind being carried in the patients' pockets. Any soiling of the delicate mechanical parts of the device may, however, call into question the operational reliability of such inhalers. However, devices of the kind described hereinbefore should present only slight resistance to the indrawn breath during inhalation. As a result, very little force is available for triggering the switching operation, and particularly the production of a foreign air pulse. Consequently, all the mechanical parts of the device are required to have an exceptionally easy action, which is not the case to the required degree in the known devices.

In view of the fact that the trigger means in known mechanisms operating with a spring bias required a sharp and almost abrupt flow of breath, DE-C 3901963 proposes a mechanical-electronic system. This system, however, requires a relatively high technical input and needs a current source.

SUMMARY OF THE INVENTION

The aim of the invention, starting from the prior art described hereinbefore, is to provide an apparatus for triggering switching operations in inhalers in synchronism with the breathing, such an apparatus being of simple construction and easy action, requiring no power supply, having no tendency to soiling as a result of its design and therefore capable of performing its function reliably for lengthy periods, even though the switching operation, being purely mechanical, is more difficult to actuate than in electronic devices.

This objective is achieved according to the invention by having the transmitter element consist of a flexible membrane clamped around its edges and incorporated in the inhaler, outside the flow path of the air during breathing in, in such a way that one side communicates with the ambient air whilst the other side is acted upon by the under pressure generated as the user breathes in through the inhaler and is associated with mechanical actuating means which operatively engage with the actuating mechanism on the switching device.

The flexible membrane is a simple transmitter element which reacts sensitively and easily to fine differences in pressure and makes reliable mechanical adjustments. It can also easily be mounted mechanically in a suitable housing. The arrangement of the membrane outside the flow path of the air which flows through the device during inhalation ensures the easy action of the membrane and its associated elements, ie. it prevents deposits of dust and dirt, and thereby guarantees reliable operation of the inhaler.

According to a further feature of the invention, the inhaler has a mouth piece with an air channel in the form of a nozzle, the connection between the membrane and mouth piece being provided by an underpressure channel the opening of which into the mouth piece is arranged in the region of maximum flow velocity.

This produces a particularly large underpressure which results in reliable switching.

According to an advantageous further feature, the switching device is designed to trigger a pump which is provided, for the purpose of generating a foreign air pulse in synchronism with the breathing, with a releasable biasing means connected to an actuating mechanism for releasing the bias, this mechanism being operatively connected to the mechanical actuating elements of the membrane transmitter.

An apparatus of this kind is versatile in use. For example, the foreign air pulse can be used to disperse a dose of a powdered medicinal substance to be inhaled in synchronism with the breathing, eg. the dose of an inhaled powder prepared on a belt-type carrier according to WO 90/13328.

A liquid can also be dispersed with the foreign air current.

Further features and possible applications of the invention will become apparent from the embodiments described by way of example and illustrated in the drawings. An inhaler having a metering device and a pump which can be triggered by the membrane transmitter as a foreign air pulse transmitter is shown by way of example, but the invention is not restricted to such applications.

DESCRIPTION OF THE PREFERRED EMBODIMENTS

Figure 1:
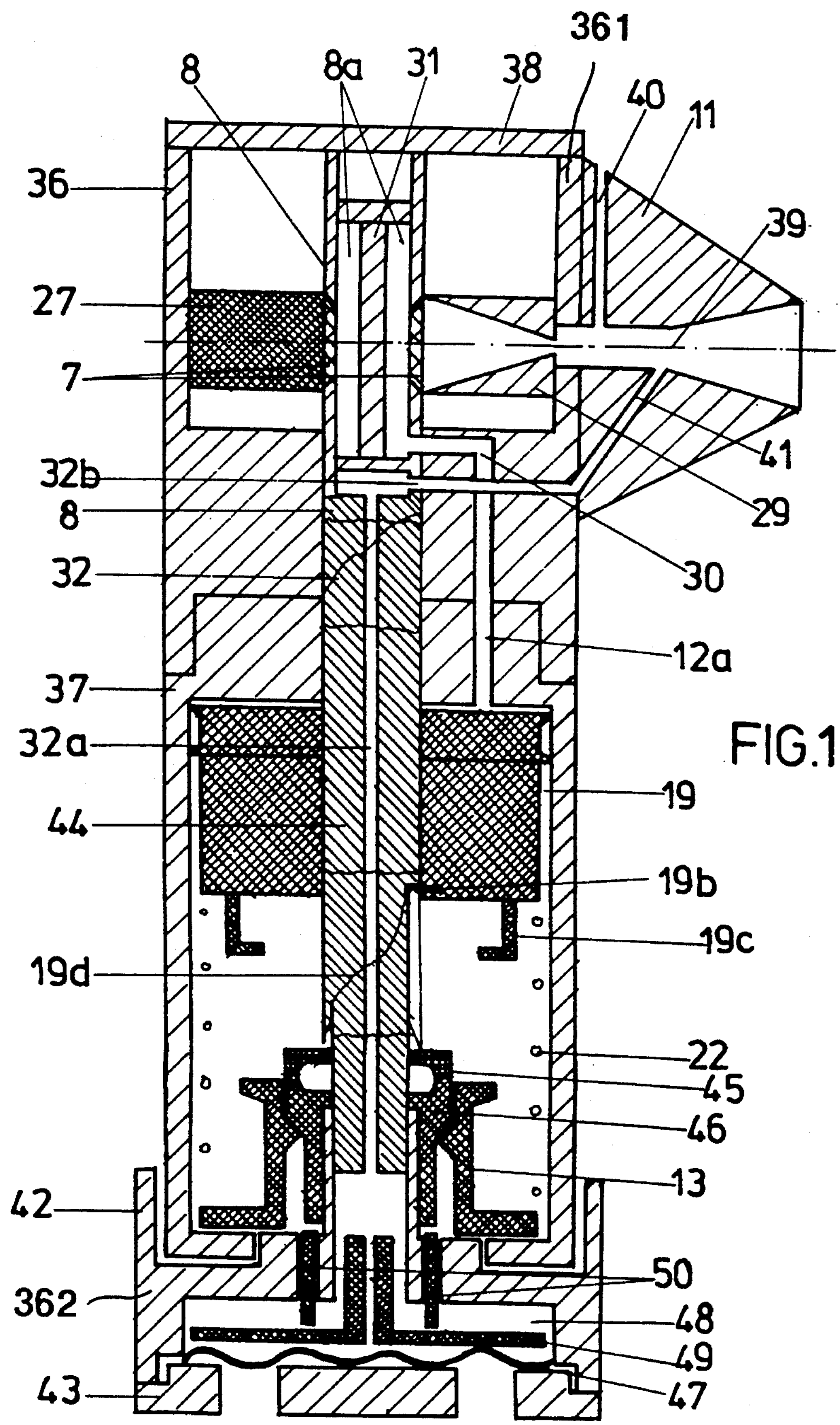
FIG. 1 shows an embodiment of a propellant-free inhaler in its normal condition shown in diagrammatic section with the device according to the invention.
Figure 2:
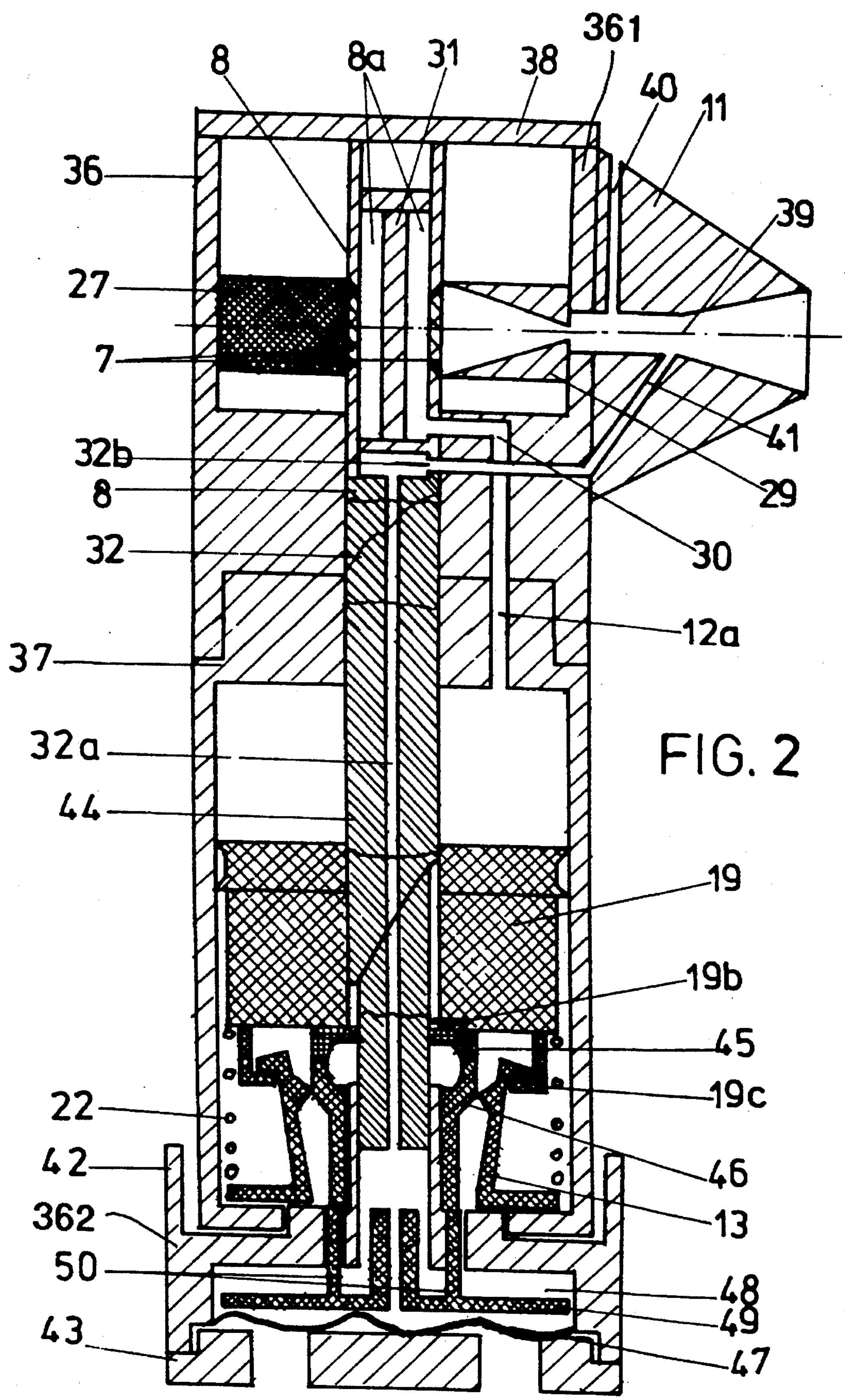
FIG. 2 shows the embodiment according to FIG. 1 ready for inhalation.

The inhaler according to FIGS. 1 and 2 has a two-part housing, namely the top housing 36, which is closed off at the top by a lid 38, and the pump housing 37 which simultaneously forms the cylinder for the piston 19 of the pumping arrangement. Both housing parts are preferably made of plastics and have conventional connecting members (not shown), eg. a screw connection.

The top housing 36 accommodates a metering device with powder dispenser 27. It has a rotatable part 8 with two metering notches 7 each of which has an associated chamber 8*a* which, being separated by a wall 31, can alternately be connected to a channel 30 so that only the metering notch which is to be "blown out" can be exposed to the dispersing jet of compressed air, via the associated chamber, from the actuable pump which will be described hereinafter. At the bottom of the part 8 is a coupling part 32 by means of which the part 8 can be connected to a rotary drive. This section of part 8 has a bore 32*b* for a low pressure channel and a longitudinal bore 32*a* for transmitting the low pressure, the importance of which will be explained hereinafter.

A dispersing nozzle 29 is connected to the metering curb 7 to be blown out and to the associated chamber in the part 8.

A mouth piece 11 which is located opposite the dispersing nozzle 29 is also mounted on the top housing to inhaler housing end portion 361 as shown in FIGS. 1 and 2. Another inhaler housing end portion 362 is also shown in FIGS. 1 and 2. The mouth piece 11 has an air channel in the form of an inhaling nozzle 39 and breathing bores 40 for the flow of external air during inhalation. The mouth piece 11 also has a low pressure channel 41 which communicates with the bore 32*b* on the part 8 and hence with the longitudinal bore 32*a*. During active breathing in, the acceleration which the air in the nozzle undergoes produces a low pressure in the nozzle and hence in the channel 41, and this low pressure continues into the longitudinal bore 32*a*. The low pressure channel is therefore expediently provided at that point in the nozzle where maximum velocity is achieved.

The pump housing 37 has a rotary knob 42 which is connected to a tensioning spindle 44 and is closed off at the end face by a cover 43 provided with bores. The tensioning spindle 44, like the part 8 to which it can be connected in accurate position and by torsional engagement with the coupling 32, has an axial bore 32*a*.

In the front part of the pump housing 37, that forms a center portion of the inhaler housing is mounted the piston pump which can be primed and triggered. The pump has the pump piston 19 which has a pin 19*b* guided in a spiral groove 19*d* of the tensioning spindle 44. In a kinematic reversal of this principle of translatory conversion of a rotary movement, cams or the like may be provided on the tensioning spindle, these cams being accommodated in a spiral groove located in the piston bore.

In FIG. 1 the piston is in the top position after triggering and expulsion of the air, whereas FIG. 2 shows the piston in the primed state. This view shows particularly clearly the pump cylinder chamber above the piston 19 in which the air is compressed by the piston as it rises. On the pump cylinder chamber is the air outlet opening and the pressure channel 12*a* which opens into the bore 30 on the part 8 in order to convey the dispersing compressed air into the appropriate chamber 8*a* or metering notch 7.

On the bottom of the piston is provided a radially symmetrical latching element 19*c*, a retaining bracket, by means of which the piston can be preloaded counter to the force of the spring 22 while engaging with an equally radially symmetrical locking bracket 13 which has resiliently yielding segments.

The superimposed parts of the retaining and locking brackets are slightly inclined, so that the retaining bracket 19*c* has a tendency, under the influence of the force of the spring 22, to bring the segments of the locking brackets inwards and thereby open the lock. The inclined surface therefore assists actuation, which is also aided by the inherent tension of the segments of the locking brackets. The latching and release mechanism or actuating mechanism also has a reset button 45 which rotates with the tensioning spindle 44, and a release button 46 with a locking shoulder which is movable in the longitudinal axial direction. When the piston is primed, the release knob 46 is pressed, by means of the reset button 45 above its locking shoulder, into the locking and release brackets 13, so that the release edge of the release brackets 13 is above the locking shoulder of the release knob 46. At the same time the locking and release brackets engage in the latching element or retaining bracket 19*c* of the piston (FIG. 2).

The edges of the reset and release knob 45 and 46 which slide over one another with a slide member are constructed in the form of a ramp. In the primed state (FIG. 2) the highest point of the ramp has already been passed, so that the space behind the end of the ramp is available for the necessary axial movement of the release knob during actuating.

The latching means shown constitute a relatively simple solution which is also mechanically easy to assemble.

For automatic actuation of the pump during active breathing in, one embodiment of the trigger mechanism according to the invention is provided which has as its central element a membrane 47 which responds to the low pressure produced in the low pressure channel 41 and extends into the axial bore 32*a*, when the patient breathes in. The membrane 47 bounds the end face of a membrane chamber 48 in which is provided a membrane pot 49 on which there are actuating pins 50 which are guided in the rotary knob 42. At their other end these actuating pins abut on the release or actuating knob 46.

In order to achieve the primed condition ready for inhalation shown in FIG. 2, starting from the unprimed rasting condition shown in FIG. 1, the following procedures should be carried out:

The rotary knob 42 is turned manually through a certain angle. The tensioning spindle 44, the reset button 45 and the part 8 rotate with the rotary knob (via the coupling 32). In the embodiment by way of example, the pitch of the spiral groove 19*d* is such that a 180° rotation is necessary in order to achieve the primed state.

By rotation of the rotary knob 42, the metering notch 7 is filled with the powder to be inhaled, initially by rotation of the part 8 in the top housing 36. Moreover, rotation of the tensioning spindle 44 causes the pin 19*b* of the piston 19 guided in the spiral groove 19*d* of the tensioning spindle to move downwards. The piston 19 thus biases the spring 22. After rotation through an angle of about 135° the piston per se is in the starting position. When the knob 42 is rotated through 45° the release button 46 is pressed into the release bracket 13 via the reset button 45 with its locking shoulder. This bracket frictionally engages in the latching element 19*c* of the piston. Spring 22, latching element 19*c*, and locking bracket 13 comprise releasable biasing means.

Thanks to this arrangement the device can be reset, in terms of metering and triggering by breath, with a single tensioning movement.

The piston is now primed and is held in position by the locking means described above. The inclined surfaces on the locking bracket 13 and on the latching element 19*c* are designed so that the latching element, under the influence of the spring force, urges the locking bracket inwards in order to open the lock. However, this is prevented by the release button 46, the thicker upper part of which presses against the cams of the locking bracket and holds them in the spread-apart position. This provides a particularly advantageous protection against accidental triggering of the device.

The inhaler is now in the state of readiness as shown in FIG. 2, ie. it is ready for inhaling.

During inhalation, as the patient breathes in through the mouth piece 11, air is supplied through the foreign air opening 40. As a result of this environmental air flowing past the bore 41 and nozzle 39, an underpressure is produced in this bore 41 which is passed on through the axial bore 32*a* into the membrane chamber 48. The atmospheric pressure prevailing through the bores in the lid 43 forces the membrane 47 inwardly onto the membrane pot 49. The latter presses on the actuating pins 50, which in turn abut on the release button 46 and, when a certain low pressure is reached, actuate the button by causing the locking shoulder of the release button 46 to be brought over the release edge (cam) of the locking bracket 13 as a result of axial movement of this button 46. The cams of the locking brackets 13 thus enter the region of the thinner shaft of the release button and are no longer able to rest on said button. Under the influence of the inherent tension of the segments of the locking brackets, which strives to bend the spring segments inwards, and under the influence of the inwardly directed force occurring on the inclined surfaces of the locking rackets and the latching element 19*c*, the segments of the locking brackets bend inwardly and the frictional engagement between the brackets and the latching element 19*c* is undone.

These double-acting forces for release advantageously ensure particularly good reliability of actuation.

The piston 19 is moved upwards by the force of the spring 22. The jet of compressed air produced is passed through the pressure channel 12*a* and passes through the bore 30 into the right hand chamber 8*a* in the metering device. The powder situated in the (right hand) metering notch 7 is dispersed through the nozzle 29 and mixed with the respiratory flow, ie. converted into an aerosol. Then the device returns to the initial state shown in FIG. 1.

The assemblies and components used in FIGS. 1 and 2 are embodiments; however, the invention is not restricted to them. Thus, for example, other construction elements may be used for converting a rotary movement into longitudinal displacement of the piston 19 and different latching and release mechanisms can be used without departing from the invention.

FIGS. 1 and 2 illustrate the advantages of the device.

The respiratory air and the foreign air have only a very short distance to travel to the mouth piece. The foreign air flows through only the metering pin and the metering chamber beforehand. The depositing of dust and dirt is therefore avoided and the components remain easy-running. If the aerosol has to be administered urgently, eg. in the event of an acute asthma attack, the device is exceptionally simple and rapid to operate.

The parts of the structure are also relatively simple and easily assembled and therefore the device can be mass produced at favourable costs.

By suitable modification which can be carried out by anyone skilled in the art the apparatus according to the invention can be adapted so as to interact with all kinds of equipment which envisage actuation triggered by breathing or synchronised with the breathing. Thus, the new device might be used, for example, in appliances such as those described in DE-A-1917911, DE-A-19455257, DE-A-3040641, DE-C-3901961, WO 90/13327, WO 90/13328, PCT GB91/00433, U.S. Pat. No. 3,921,637, U.S. Pat. No. 3,187,748 or U.S. Pat. No. 4,648,393, without restricting the application of the invention to these types of equipment.

We claim:

1. Device for use in an inhaler, comprising:

a transmitter element responsive to a low pressure produced as a user breathes in a main air current having a flow path through the inhaler;

a switching device comprising an actuating mechanism operatively connected to said transmitter element, said transmitter element comprising a flexible membrane clamped around its edges and disposed within the inhaler outside the flow path of the main air current so that one side of said membrane is exposed to ambient air and the other side of said membrane is acted upon by the low pressure produced as the user breathes in, said membrane defining one side of a membrane chamber;

a membrane pot disposed within said membrane chamber;

an actuating pin partially disposed within said membrane chamber, wherein said membrane moves onto said membrane pot in response to the low pressure so that said membrane pot presses on said actuating pin to thereby actuate said actuating mechanism; and a pump triggered by said switching device for generating a pulse of foreign air in synchronism with breathing of the user, said pump including releasable biasing means connected to said actuating mechanism for releasing the bias, said actuating mechanism operatively connected to said membrane pot and said actuating pin.

2. Device according to claim 1, wherein said pump comprises a pump chamber with an air outlet channel and a pump piston which can be biased by manual actuation counter to the force of a spring and can be latched on the side of said pump chamber which is remote from said air outlet channel.

3. Device according to claim 2, further comprising:

an actuating knob;

a radially symmetrical locking bracket; and a radially symmetrical retaining bracket mounted on the end of said piston remote from said pump chamber, said retaining bracket having an inclined retaining surface which, when said piston is tensioned by means of said actuating knob, can be brought into operative connection with an inclined surface of said locking bracket which has resiliently yielding segments connected with said actuating pin by means of said actuating knob so that when said membrane responds in synchronism with the breathing said actuating knob can be at least partially pushed out of said locking bracket, thereby reversing the spreading of said segments of said locking bracket.

4. Device according to claim 3, wherein said actuating knob has a radially thickened portion with a shoulder projection and said locking bracket has an encircling edge so that in the biased condition of said piston said edge abuts said thickened portion.

5. An inhaler, comprising:

a housing having a first end portion, a second end portion, and a center portion;

a mouth piece laterally secured to said first end portion;

a metering device disposed within said first end portion for metering an active substance to be inhaled;

a transmitter element disposed within said second end portion which responds to a low pressure produced as a user breathes in through the inhaler, and transmitter element comprising a flexible membrane having one side exposed to ambient air and the other side of said membrane acted upon by the low pressure produced as the user breathes in through the inhaler, said membrane defining one side of a membrane chamber, a membrane pot disposed within said membrane chamber, an actuating pin partially disposed within said membrane chamber, and an actuating mechanism, wherein said membrane moves onto said membrane pot in response to the low pressure so that said membrane pot presses on said actuating pin to thereby actuate said actuating mechanism;

a pump disposed within said center portion for generating a pulse of foreign air in synchronism with breathing of the user, said pump including releasable biasing means connected to said actuating mechanism.

6. Inhaler according to claim 5, further comprising:

a low pressure channel which extends from said mouth piece through said housing to said membrane.

7. Inhaler according to claim 5, wherein said pump comprises a pump chamber with in air outlet channel and a pump piston which can be biased by manual actuation counter to the force of a spring and can be latched on the side of said pump chamber which is remote from said air outlet channel.

8. Inhaler according to claim 7, further comprising:

an actuating knob;

a radially symmetrical locking bracket; and a radially symmetrical retaining bracket mounted on the end of said piston remote from said pump chamber, said retaining bracket having an inclined retaining surface which, when said piston is tensioned by means of said actuating knob, can be brought into operative connection with an inclined surface of said locking bracket which has resiliently yielding segments connected with said actuating pin by means of said actuating knob so that when said membrane responds in synchronism with the breathing said actuating knob can be at least partially pushed out of said locking bracket, thereby reversing the spreading of said segments of said locking bracket.

9. Inhaler according to claim 8, wherein said actuating knob has a radially thickened portion with a shoulder projection and said locking bracket has an encircling edge so that in the biased condition of said piston said edge abuts said thickened portion.

* * * * *